US005574619A

United States Patent [19]

Jeong

[11] Patent Number: 5,574,619

[45] Date of Patent: Nov. 12, 1996

[54] APPARATUS FOR GENERATING ANIONS IN VIDEO APPLIANCES

[75] Inventor: Seok H. Jeong, Kyungsanbuk-Do, Rep. of Korea

[73] Assignee: LG Electronics Inc., Seoul, Rep. of Korea

[21] Appl. No.: 410,276

[22] Filed: Mar. 24, 1995

[30] Foreign Application Priority Data

Mar. 24, 1994 [KR] Rep. of Korea ........................ 94-5933

[51] Int. Cl.[6] .................................................... H01T 23/00

[52] U.S. Cl. .......................... 361/230; 361/213; 361/229; 361/231

[58] Field of Search .................................... 361/212, 213, 361/222, 225, 229, 230–232; 250/324

[56] References Cited

U.S. PATENT DOCUMENTS 3,469,031 9/1969 Setchell .............................. 361/231 X
5,153,811 10/1992 Rodrigo et al. ......................... 361/231
5,241,449 8/1993 Moeller et al. ......................... 361/231

FOREIGN PATENT DOCUMENTS 156930 6/1954 Australia .
2452824 5/1976 Germany .
392873 5/1933 United Kingdom .

*Primary Examiner*—Fritz Fleming
*Attorney, Agent, or Firm*—Helfgott & Karas, P.C.

[57] ABSTRACT

The invention releases anions out of a main body using convection caused by heat from heating elements inside a product without a fan or a blower. To make up for reduction of the amount of released anions due to elimination of the fan, the apparatus according to the present invention can be drawn out from a main body so as to maximize the amount of released anions.

10 Claims, 3 Drawing Sheets

1
2
4
5
5A
5B
6
7
8
9
10
11
11B
12
13
14
15
16
16A
17
18
19
20
21

APPARATUS FOR GENERATING ANIONS IN VIDEO APPLIANCES

BACKGROUND OF THE INVENTION

1. Field of the Invention

The present invention relates to an apparatus for generating anions in video appliances, which releases anions out of the appliance, using convection caused by heat from heating elements in the appliance.

2. Description of the Related Art

Several video appliances, such as a television receiver, a computer monitor, an audio/video system, etc., are usually used in a limited space. Thus, environmental problems arise from their use. That is, users of the appliances are exposed to an environment tainted with contaminates, such as dust, air pollution, cigarette smoke or the like.

Meanwhile, recently developed video appliances, having an apparatus for generating anions, create and release anions while performing their own functions, improving the environment.

Conventional video appliances which have an apparatus for generating anions, use an exhaust fan to release anions. This is the so-called forced blowing method.

However, such a method results in other problems. One is fan noise, which creates another environmental problem. Another is the necessity of adding extra components, e.g., the fan and circuitries to drive the fan. The additional components make it difficult to use the interior space of a product optimally. This is also contrary to the growing tendency to miniaturize products.

Finally, the cost that is spent on ancillary functions instead of primary functions will be increased. Aside from the increased cost of production due to the added components, there is an increase in power consumption, design cost, manufacturing cost, etc.

SUMMARY OF THE INVENTION

It is an object of the present invention to provide an apparatus for generating anions in video appliances, which releases anions utilizing convection caused by heating elements or heat sinks rather than an exhaust fan.

To compensate for a reduction in the amount of released anions due to the elimination of the fan, the present invention also provides an apparatus which can be drawn out from a main body to maximize the amount of released anions.

According to one feature of this invention, there is provided an apparatus for generating anions in video appliances, comprising:

means for releasing anions including an anion generator, an air conduit for inducing an ascending air stream caused by heat from heating elements inside said video appliance so as to release said ascending air stream, and a ventilation hole, provided between said anion generator and said air conduit, for leading a part of said ascending air stream to said anion generator; and means, positioned on a part of said video appliance, for supporting said anions releasing means.

According to another feature of this invention, there is provided an apparatus for generating anions, comprising:

an air chamber in which an ascending air stream caused by heat from heating elements inside said video appliance penetrates from a lower part to an upper part;

an anion creating chamber contiguous to said air chamber; and a high-voltage generator for providing a high voltage necessary for creation of anions.

BRIEF DESCRIPTION OF THE DRAWINGS

The above object and other advantages of the present invention will become more apparent by describing the preferred embodiment of the present invention with reference to the attached drawings, in which.

DETAILED DESCRIPTION OF THE PREFERRED EMBODIMENT

Figure 1:
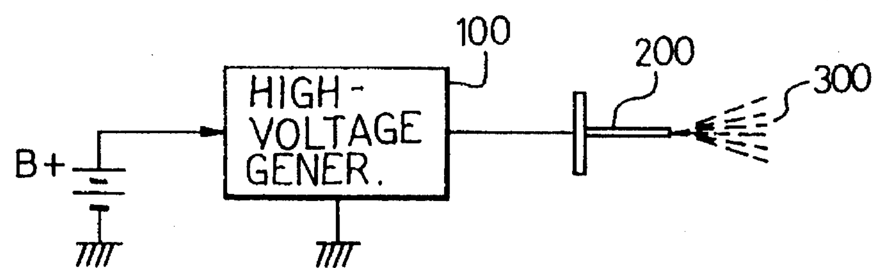
FIG. 1 is a conceptual view indicating a general apparatus for generating anions.

Typically, as to generation of anions, as shown in FIG. 1, a high-voltage generator 100 provides a source of high DC voltage (B+), and applies the high voltage to a discharge needle 200 to perform a corona discharge. As the corona discharge ionizes the surrounding air, anions 300 are created, and emanate from a main body of a product.

Figure 2:
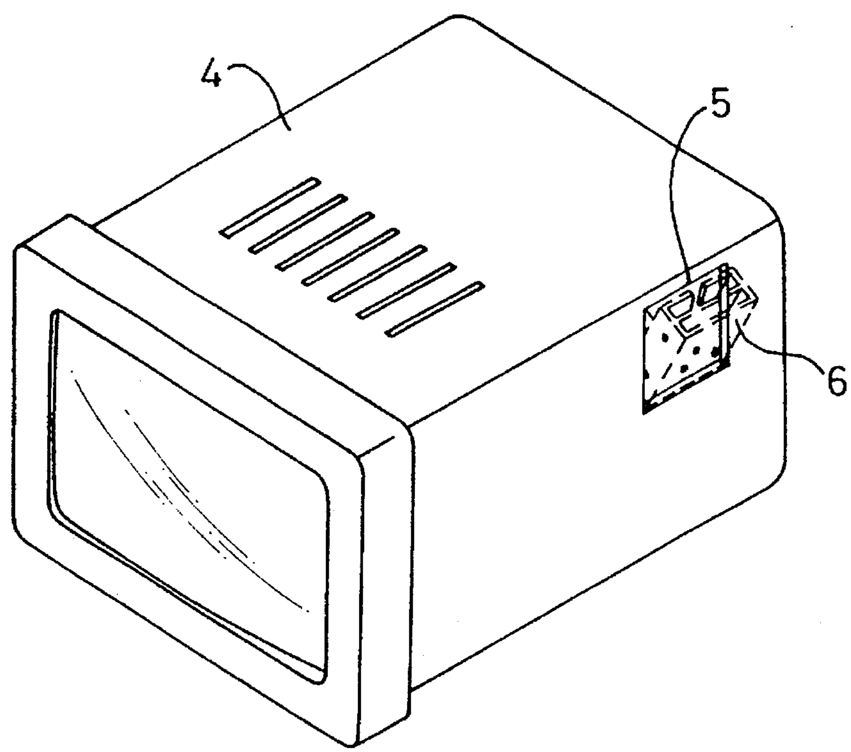
FIG. 2 is a perspective view showing a computer monitor adopting an apparatus for generating anions according to the present invention.

An apparatus for generating anions in video appliances, the present invention, adapted to a computer monitor is indicated in FIG. 2.

In FIG. 2, a supporting section 5 is inwardly prepared on a housing 4 of a main body. An apparatus for, generating anions 6 is assembled in the supporting section 5.

Figures 3A, 3B, 3C:
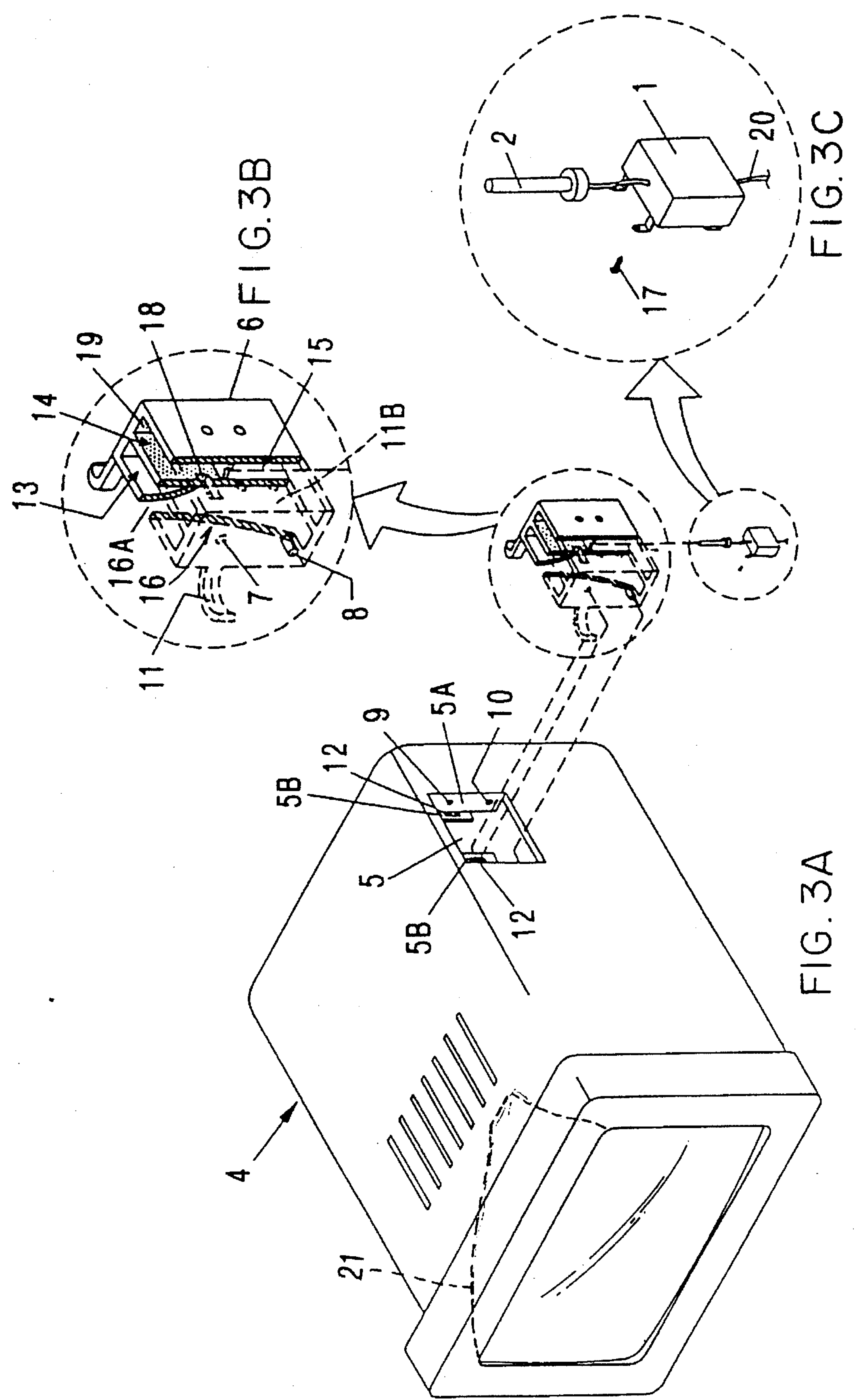
FIG. 3 is an exploded view of the apparatus depicted in FIG. 2.

A detailed structure is shown in FIG. 3.

Two hemispheric projections 7 and two shafts 8 are prepared on both sides of the apparatus for generating anions 6 to fix the apparatus 6 to the supporting section 5. It is often desirable that the central parts of the shafts 8 are axially D-cut for easy insertion.

Two recesses 9 in which the projections 7 are latched and two bearings 10 in which the shafts 8 are held, are provided on both inner sides 5A of the supporting section 5.

Two elastic hooks 11 are formed projectingly from the back of the apparatus for generating anions 6 to prevent the apparatus 6 from departing from the supporting section 5.

At the back wall 5B of the supporting section 5, joining grooves 12 are prepared, in which the hooks 11 are joined.

By combining the hooks 11 with the grooves 12 and the shafts 8 with the bearings 10, the apparatus for generating anions 6 is safely mounted in the supporting section 5, which the apparatus 6 is pivotally movable centering around the shafts 8. The hooks 11 play a part in preventing the apparatus for generating anions 6 from being detached from the supporting section 5 when the apparatus 6 moves.

The hemispheric projections 7 are inserted into the recesses 9 to fix the apparatus for generating anions 6 at its regular position. Thereby the apparatus 6 cannot itself be opened.

If a user pulls out the apparatus 6 in order to detach the projections 7 from the recesses 9, the apparatus 6 is drawn out from the housing as shown in FIG. 2.

Figure 4:
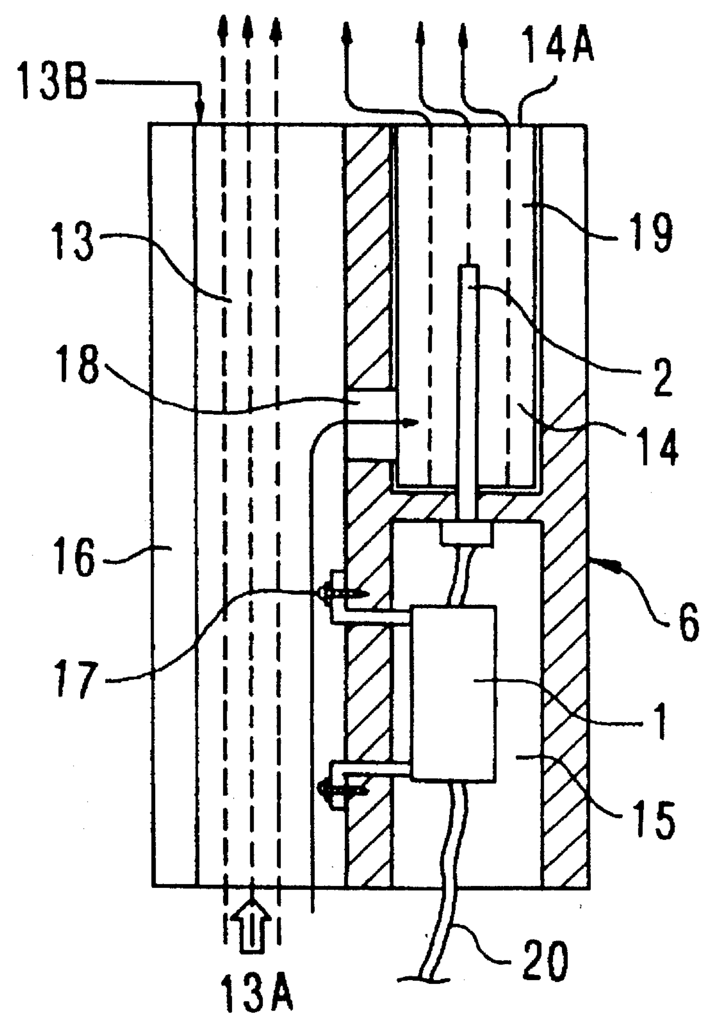
FIG. 4 is a longitudinal sectional view of an apparatus of the present invention.

In the apparatus for generating anions 6, as shown in FIG. 4, there are several elements including an air chamber 13 for inducing an air stream, an anion chamber 14 in which anions are created by a corona discharge, and a high-voltage chamber 15 for generating a high voltage.

The upper part of air chamber 13 serves as an exit 13B; its lower part as an entrance 13A. A side wall 16 is formed as a funnel.

A high-voltage discharge needle 2 and a high-voltage generator 1 are equipped in the anion chamber 14 and in the high-voltage chamber 15, respectively.

A ventilation hole 18 is perforated through a wall between the air chamber 13 and the anion chamber 14. An anticharge agent 19 is coated on the inner surface of the anion chamber 14 to prevent electrodeposition of anions. A power supply wire 20 is connected to the high-voltage generator 1. Generator 10 is fixedly attached to the apparatus 6 via screw 17.

The operation of such a constructed apparatus will be described.

When applying the power source, if a user pulls out the apparatus for generating anions 6 from the supporting section 5, the apparatus 6 is aslant drawn from the supporting section 5 to the outside.

From the power source, the high-voltage generator 1 generates a high voltage and applies the high voltage to the discharge needle 2. Thereafter a corona discharge between the discharge needle 2 and the air ionizes the surrounding air to create anions. The created anions are released to a room through the exit 14A.

An ascending air stream is formed in a main body by convection caused by heat radiated from heating elements in the main body. The heating elements include all electronic components in the video appliance that generate heat when operational. For example, picture tube 21 in housing 4 is one of several possible heating elements. This air stream is led to the air chamber 13 and exits towards the air.

The ascending air stream, entering the entrance 13A and exiting the exit 13B of the air chamber 13, increases the release efficiency of anions released from the anion chamber 14. Especially, the ascending air stream, led to the anion chamber 14 through the ventilation hole 18, lets the anions emanate more vigorously.

Preferably the side wall 16 of the air chamber 13 is funnel-shaped (see FIG. 3), comprising a narrow portion 16A at the top and a wide portion 16B at the bottom of side wall 16. The funnel-shaped side wall 16 induces a Bernoulli effect of the ascending air stream, which causes the velocity of the air at the exit 13B to increase so that the air emanating from exit 14A of the anion chamber 14 are drawn (see FIG. 4) towards the exit 13A of the air chamber 13. Thereby the anions are released more quickly and forcefully from the anion chamber 14 to an exterior room.

The anticharge agent 19 prevents the anions from electrodepositing on the inner surface of the anion chamber 14.

As a result, this invention releases anions out of a main body using convention occurring due to heat from heating elements inside the body, even without a fan and fan driver.

To compensate for reduction of the amount of released anions due to elimination of a fan, the apparatus according to the present invention has been designed to be able to be exposed to the peripheral airs when used, which maximizes the amount of released anions.

What is claimed is:

1. A single unit apparatus for generating anions, comprising:

an air chamber in which an ascending air stream caused by heat from heating elements inside a video appliance penetrates from a lower part to an upper part;

an anion chamber contiguous to and sharing a common wall with said air chamber;

a ventilation hole between the air and anion chambers for permitting a portion of said ascending air stream to travel from said air chamber to said anion chamber; and a high-voltage generator for providing a high voltage necessary for creation of anions.

2. An apparatus for generating anions according to claim 1, wherein said air chamber has a side wall which is funnel-shaped so as to induce a Bernoulli effect of said ascending air stream.

3. An apparatus for generating anions according to claim 1, wherein an anticharge agent is coated on an inner surface of said anion chamber to prevent electrodeposition of anions.

4. A single unit apparatus for generating anions in an electronic appliance, said unit at least partially extending into the interior of said appliance, comprising:

an air chamber having an air conduit for inducing an ascending air stream caused by heat from heating elements inside said appliance, an exit positioned at the top of said chamber for releasing said ascending air stream, and a ventilation hole positioned at a side of said chamber for permitting a portion of said ascending air stream to release out said hole; and an anion chamber positioned adjacent to said air chamber such that said ventilation hole extends from said air chamber to said anion chamber, through a common wall, permitting said portion of ascending air stream to enter said anion chamber, said anion chamber having an anion generator for forming said anions.

5. The apparatus according to claim 4, wherein said electronic appliance is a video appliance.

6. The apparatus according to claim 5, including means for supporting said apparatus to a portion of said video appliance.

7. The apparatus according to claim 6, further including front and rear walls and left and right side walls.

8. The apparatus according to claim 7, wherein the supporting means comprises:

hemispheric projections on the upper parts of said left and right side walls for latching said apparatus to said video appliance via recesses in said video appliance;

shafts on the lower parts of said side walls; and bearings in which said shafts are held.

9. The apparatus according to claim 8, wherein said apparatus is pivotally supported by the supporting means, such that said apparatus can be removed from and replaced in said video appliance.

10. The apparatus according to claim 8, wherein the supporting means further comprises fixing hooks on the edges of said rear wall contiguous to said left and right side walls for further securing said apparatus to said video appliance via joining grooves in said appliance.

* * * * *